US008982455B2

(12) United States Patent
Redford (10) Patent No.: US 8,982,455 B2
(45) Date of Patent: Mar. 17, 2015

(54) MODULAR DESIGN OF A SCANNING MICROSCOPE ATTACHMENT AND ACCESSORIES

(75) Inventor: Glen Ivan Redford, Arvada, CO (US)

(73) Assignee: Intelligent Imaging Innovations, Inc., Denver, CO (US)

( * ) Notice: Subject to any disclaimer, the term of this patent is extended or adjusted under 35 U.S.C. 154(b) by 567 days.

(21) Appl. No.: 12/887,832

(22) Filed: Sep. 22, 2010

(65) Prior Publication Data

US 2011/0072543 A1    Mar. 24, 2011

Related U.S. Application Data

(60) Provisional application No. 61/244,555, filed on Sep. 22, 2009.

(51) Int. Cl.
*G02B 21/18*    (2006.01)
*G02B 21/00*    (2006.01)
*G01N 21/01*    (2006.01)

(52) U.S. Cl.
CPC ............. *G02B 21/002* (2013.01); *G02B 21/18* (2013.01); *G01N 2021/015* (2013.01)
USPC ........ 359/372; 359/381; 359/382; 359/197.1; 359/198.1

(58) Field of Classification Search
CPC ....... G01Q 60/08; G01Q 60/02; G01Q 60/04; G01Q 60/06; G01Q 60/00; G01N 21/01; G02B 21/00
USPC .......................................... 359/368, 381, 384
See application file for complete search history.

(56) References Cited

U.S. PATENT DOCUMENTS

| | | | | |
|---|---|---|---|---|
| 4,784,488 | A * | 11/1988 | Doyle et al. .................. | 356/455 |
| 6,144,031 | A * | 11/2000 | Herring et al. ................ | 250/352 |
| 6,977,773 | B2 * | 12/2005 | Engelhardt et al. ........... | 359/381 |
| 7,224,523 | B2 * | 5/2007 | Fukuyama et al. ........... | 359/385 |
| 7,483,207 | B2 * | 1/2009 | Storz et al. .................... | 359/390 |
| 2002/0159144 | A1 * | 10/2002 | Engelhardt et al. ........... | 359/385 |
| 2005/0226570 | A1 * | 10/2005 | Togami et al. ................. | 385/92 |
| 2006/0153503 | A1 * | 7/2006 | Suzuki et al. ................. | 385/53 |
| 2008/0088918 | A1 * | 4/2008 | O'Connell .................... | 359/371 |

\* cited by examiner

*Primary Examiner* — Thomas K Pham
*Assistant Examiner* — Marin Pichler
(74) *Attorney, Agent, or Firm* — Jason H. Vick; Sheridan Ross, PC (57) ABSTRACT

A modular laser scanning system where the laser scanner and various optical "building blocks" are contained in separate mechanical and optical modules. These modules can be combined to provide flexible systems with unique laser scanning capabilities or combinations of techniques. Additionally, the combining of these modules is achieved through the use of a mechanical and optical coupling standard.

25 Claims, 8 Drawing Sheets

MODULAR DESIGN OF A SCANNING MICROSCOPE ATTACHMENT AND ACCESSORIES

RELATED APPLICATION DATA

This application claims the benefit of and priority under 35 U.S.C. §119(e) to U.S. patent application No. 61/244,555, filed Sep. 22, 2009, entitled "Modular Design of a Scanning Microscope Attachment and Accessories," which is incorporated herein by reference in its entirety.

BACKGROUND

Laser scanning technology is increasingly used in the biomedical research field. There exist several commercial laser scanning microscopes for optical sectioning. Laser scanners are also used in conjunction with laser scanning microscopes or widefield microscopes to provide a way to manipulate a sample at a point or defined region while imaging.

In addition laser scanners are used for several advanced techniques such as two-photon (2p) imaging, fluorescence lifetime imaging (FLIM), fluorescence correlation spectroscopy (FCS), optical traps, and several others. Typically these advanced techniques are realized on systems designed for that specific technique.

SUMMARY

Increasingly there is a need for systems that can combine these advanced techniques as well as incorporate more typical imaging methods. For example, a system that could seamlessly provide FCS information from an area of a live fluorescence image would be very useful. Also important is that such systems would be more usable by the biologists who would most benefit from the advanced techniques, while a custom system that only provides that advanced technique would be more challenging.

One exemplary aspect of this invention generally relates to laser scanning in optical microscopes. More specifically, an exemplary embodiment of this invention relates to a laser scanning device. Even more specifically, an exemplary embodiment of the invention relates to a modular laser scanning device with accompanying modular optical components intended to extend the functionality of standard optical microscopes. Even more specifically, an exemplary embodiment of the invention relates to a mechanical and optical mounting standard that enables the modular nature of the subcomponents of a laser scanning system.

In accordance with an exemplary embodiment, a laser scanning attachment for an optical microscope generally includes a laser input, a scanning device, and optics to couple the scanned laser into the microscope. The laser input can include an aperture for injecting a direct laser beam or it can be coupled to, for example, an optical fiber with the appropriate optics. The scanning device is often a resonant or non-resonant galvanometer mirror system although there are many other ways of scanning the laser beam. A modern optical microscope has several points where the scanned beam can be injected so that the laser reaches the sample. The most important of these are the document ports and the epi-illumination port. There are also other means of injecting the scanned beam, but they typically require a specialized microscope or modification of a standard microscope.

In one exemplary basic form, a device for adding laser scanning techniques to a standard microscope can be thought of in three basic components. The heart of the device is the scanner itself. The scanner then has an optical system between it and the microscope (inner optics). On the other side of the scanner there is another optical system (outer optics). The outer and inner optics change depending on the location of the scanner relative to the microscope and depending upon the desired technique. For example, coupling the scanner to an epi-port for photo-bleaching could just be a single lens for the inner optics (not including the microscope's internal optics) and a fiber coupler for the outer optics. A more complex example could use the scanner for 2p imaging on a document port—this would require a mirror relay for the IR laser for the outer optics and a long pass dichroic with a detector and several lenses for the inner optics. Having multi-function systems would increase the complexity of the two optical parts.

If the scanner and its various optical accompaniments were modular (in that they include separate mechanical pieces that are combinable) it would simplify the manufacture of the components and be more flexible in its use. Each module would provide a single (or more than one) optical function. For example, the optics for coupling the scanner to a given location on a microscope would be one module; the optics and dichroic for splitting the image into two optical paths would be another module. Providing a solution for a specific technique is then just a matter of combining the correct modules. Not only is such an arrangement flexible it is also highly extensible, making available new techniques or combinations of techniques. This is useful because a specific biological research lab may require a combination of techniques that are unique for this lab. Most commercial entities would be hesitant to develop an instrument that would only be sellable to that lab. With this modular design, the solution could be provided with standard list items. If something truly unique were required, it would perhaps only mean the creation of a new module or modification of an existing one—either being much easier and cheaper that redesigning an entire system.

Accordingly, one exemplary embodiment of the invention is directed toward a modular laser scanning system. The laser scanner is a single module that with various inner and outer optic modules that provide a complete laser scanning attachment for a microscope. This will allow the addition of laser scanning techniques to the already available techniques on the microscope. Importantly, the laser scanning system and the software that control the system can be designed to work seamlessly with the microscope.

An important consideration for creating such a modular system is the mechano-optical coupling used between the modules. There are several existent standards for such coupling, one of the most common being the c-mount system. The c-mount standard includes the mechanical coupling and the location of the image plane relative to the mechanical mount. It also specifies the optical aperture near the image plane. There are a couple of disadvantages to the c-mount standard including the rotational freedom of the mounting, lack of mechanical strength for larger lateral forces, and an image plane that is located outside of the actual mechanical coupling. The last is only a disadvantage because it causes a disparity between the two genders of the coupling which can be troublesome with bidirectional optical systems. An additional failing of the c-mount standard is that there is no standardization of the field or of the incident angle for the image. Ideally, a mechano-optical coupling standard would be more stable, rotationally stabilized, with an image plane directly between the modules to be coupled. For more precise, complex optical systems, the field and incident angle need to be strictly specified as well.

Practically, any standard used would be required to interface with the c-mount standard as it is so prevalent for detectors, etc.

One exemplary mechano-optical coupling standard would be a polygonal insert in a matching flange where after insertion, the two parts can be securely fastened together (with a bolt or other fastener or fastening system, for example). The simplest and most practical standard would be a square insert in a square flange (described in more detail herein below). Throughout the mounts there is a 25 mm optical aperture, and the image plane is located directly between the two devices. Additionally, this standard would allow the two devices to rotate relative to each other at 90 degree intervals. This allows the mechanical flexibility needed for complex combinations of these modules. This standard has the following exemplary specifications: 1) the maximum field is 12 mm in diameter, 2) the maximum incident angle is 6.8 deg, 3) the image location is in the center of the mounting flange.

Many standards with variations on the mechanical coupling used and the optical specifications would also adequately meet the needs of exemplary embodiments of this invention. The exemplary embodiments of the invention are intended to include any and all such modifications of the mounting standard.

The exemplary apparatus can comprise of the following modules:

a resonant, galvo scanner, a dual galvo scanner, an inner optical module for connecting to the epi port of a microscope, an inner optical module for connecting to the document port of a microscope, an outer optical module for accepting a fiber input from a laser, a dichroic for splitting an optical path by spectrum, a fast switcher for splitting an optical path, a detector such as a PMT (Photomultiplier) or APD (avalanche photodiode array), an outer module with pinholes for confocal imaging, a filter wheel and a spherical aberration correction device. However, it is to be appreciated that this list is not all inclusive as other modules can be conceived and integrated into the system.

These modules can be combined into a very large number of configurations for providing multiple laser scanning techniques and unique functionality. When combined, an attachment is created for a microscope that will add laser scanning functionality to the microscope without affecting the normal function of the microscope.

Aspects of the invention are thus directed towards laser scanning in a microscope.

Still further aspects of the invention are directed toward a laser scanning device.

Even further aspects of the invention are directed toward a modular laser scanning device with accompanying modular optical components intended to extend the functionality of standard optical microscopes.

Even further aspects of the invention are directed toward a collection of modules including a scanner that add laser scanning functionality to a microscope such that various techniques and perhaps new unique techniques can be combined and added to the microscope.

Still further aspects of the invention relate to an apparatus for combining optical modules including: a laser scanner, a mechanical coupling standard between the modules, an optical coupling standard between the modules, means for controlling the various modules in a synchronized fashion, means for coupling the combined modules to the various ports on a microscope, means for coupling the combined modules to the various brands and styles of microscopes.

The aspect above, where the laser scanner is a dual galvo scanner.

The aspect above, where the laser scanner is a resonant scanner.

The aspect above, where the laser scanner is some other type or means of laser scanning.

The aspect above, where the multiple laser scanners are combined.

The aspect above, where the motorization control device is synchronized with the detector.

The aspect above, where the apparatus is combined with an optical microscope.

The aspect above, where the apparatus is combined with an electronic imaging device such as a camera.

The aspect above, where the apparatus is combined with a scanning microscope.

The aspect above, where the scanning microscope is a confocal microscope.

The aspect above, where the scanning microscope is a two-photon microscope.

Even further aspects of the invention are directed toward a laser scanning device comprising a laser scanner contained in a separate mechanical entity.

Any of the above aspects further comprising a mechanical and optical standard for coupling the laser scanner and one or more additional optical modules.

Any of the above aspects further comprising a separate module for attaching the laser scanner to a microscope.

Any of the above aspects, wherein the attachment is made to a document port of the microscope.

Any of the above aspects, wherein the attachment is made to an EPI port of the microscope.

Any of the above aspects, wherein the separate module also contains optics necessary for coupling to the microscope.

Any of the above aspects, further comprising separate modules containing optics for one or more of adjusting the functionality of the laser scanning device, combining multiple scanners and multiple techniques.

Any of the above aspects, wherein one module comprises fiber coupling mechanics and optics for coupling to a laser.

Any of the above aspects, wherein one module comprises a path switcher to split the optical pathway into several pathways.

Any of the above aspects, wherein the path switcher contains a fast galvanometer.

Any of the above aspects, wherein the path switcher provides an imaging bypass for attaching a camera to the same port as the laser scanner.

Any of the above aspects, wherein one module is a dichroic path splitter that spectrally splits the optical path.

Any of the above aspects, wherein one module is a spherical aberration correction device.

Any of the above aspects, wherein one module is a filter wheel.

Any of the above aspects, wherein one module is a detector or a PMT.

Any of the above aspects, wherein the standard allows rotational freedom only on 90 degree intervals.

Any of the above aspects, wherein an additional module provides a technique related to laser scanning or coupling of the system with a microscope.

Even further aspects relate to a scalable modular system that separates optical functions applicable to a laser scanning device into separate mechanical entities, each mechanical entity being combinable in different orders and amounts to enable different functionality in the laser scanning system.

Any of the above aspects, wherein the standard includes a polygonal flange and insert system that are rigidly combined.

Any of the above aspects, wherein an image plane in the standard lies directly between the two combined modules.

Any of the above aspects, wherein the polygon is a square.

Any of the above aspects, further comprising a defined field and incident angle for the standard.

These and other features and advantages of this invention are described and, or are apparent from, the following detailed description of the exemplary embodiment.

BRIEF DESCRIPTION OF THE DRAWINGS

The exemplary embodiments of the invention will be described in detail, with reference to the following figures wherein:

FIG. 18 illustrates an environmental perspective view and

FIG. 19 a graphical representation of a complex system using a plurality of modules.

DETAILED DESCRIPTION

The exemplary embodiments of this invention will be described in relation to microscopes, imaging systems, and associated components. However, it should be appreciated that, in general, known components will not be described in detail. For purposes of explanation, numerous details are set forth in order to provide a thorough understanding of the present invention. It should be appreciated however that the present invention may be practiced in a variety of ways beyond the specific details set forth herein.

Figure 1:
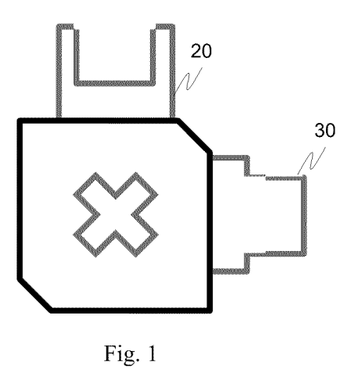
FIGS. 1-9 illustrate graphical representations of some of the possible modules that would work with exemplary embodiments of the laser scanning system.
Figure 2:
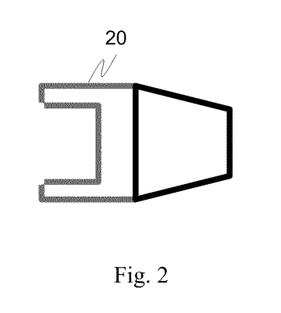
Figure 3:
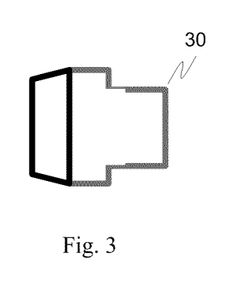
Figure 4:
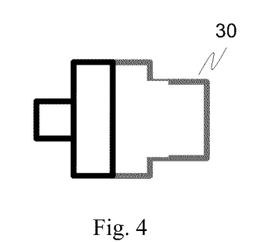
Figure 5:
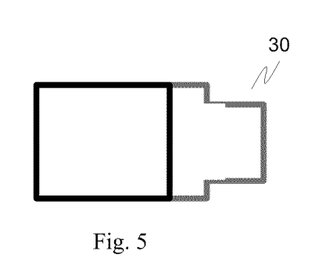
Figure 6:
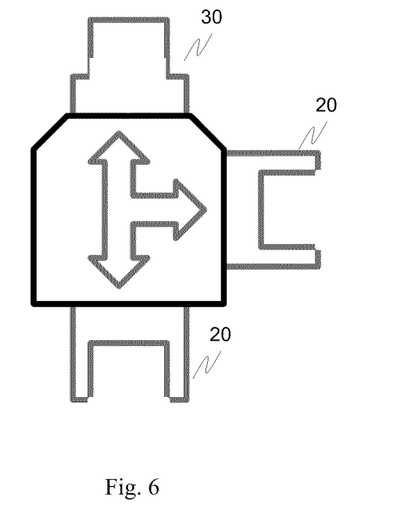
Figure 7:
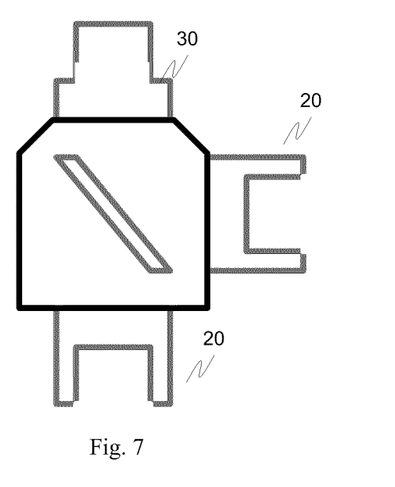
Figure 8:
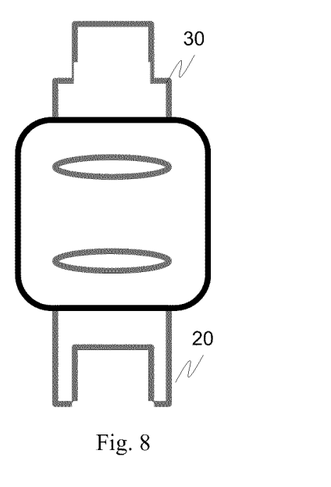
Figure 9:
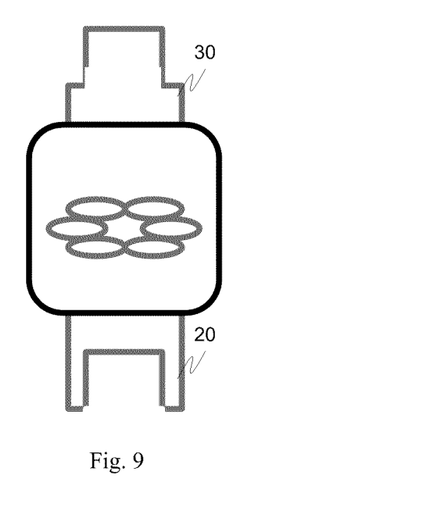

FIGS. 1-9 illustrate graphical representations of several possible modules that can be used with the exemplary embodiments of invention thereby providing the modular, scalable scanning microscope. Illustrated in FIG. 1 is a scanner, in FIG. 2 a male c-mount adapter, in FIG. 3 a female c-mount adapter, in FIG. 4 a fiber input, in FIG. 5 a detector, in FIG. 6 a fast port switcher, in FIG. 7 a dichroic beam splitter, in FIG. 8 a spherical aberration correction device and in FIG. 9 a filter wheel. On each of these is represented a connectable flange 20 and/or insert 30 (described in greater detail herein below) that allow any one or more of the modules to be interconnected.

Figure 10:
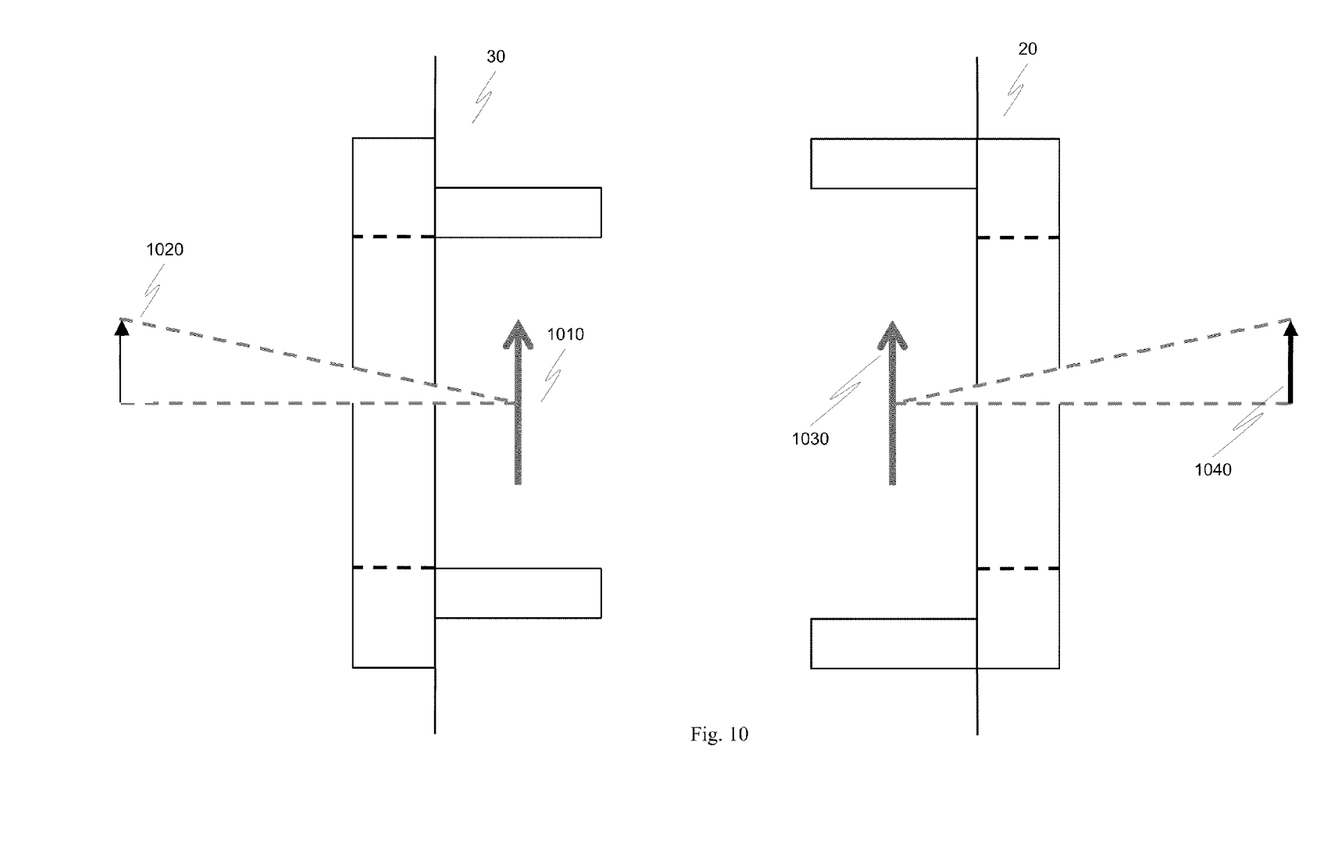
FIG. 10 illustrates an exemplary mounting standard.
Figure 11:
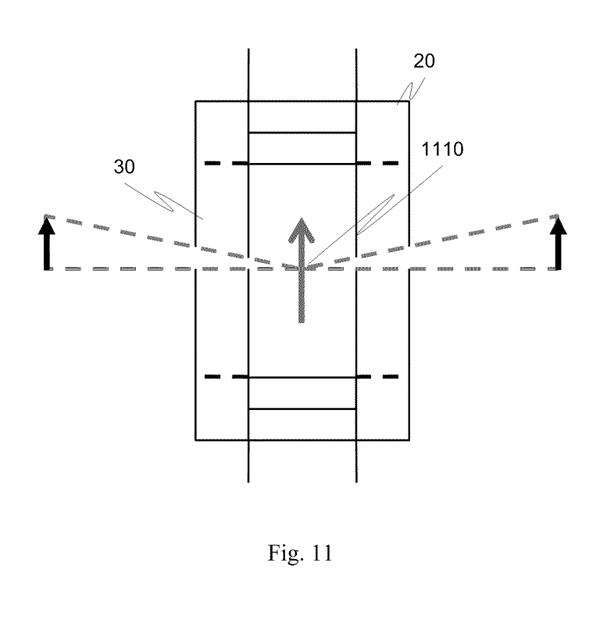
FIG. 11 illustrates the exemplary mounting standard of FIG. 10, with the male and female portions thereof interconnected.

FIG. 10 illustrates a detailed graphical representation of an exemplary mounting standard that includes a flange 20 and an insert 30. The flange 20 and an insert 30 can be mounted to any of the above described modules, or in general to any module. The image plane 1010 is located within the insert 30 with a given incidence angle 1020. The image plane 1030 is located within the flange 20 with a given incidence angle 1040. The insert 30 couples with the flange 20 which allows the connection of a module associated with the insert 30 to another module that is associated with the flange 20. When the insert 30 and flange 20 are joined (as illustrated in FIG. 11) the image plane 1110 lies directly between the two modules.

Figure 12:
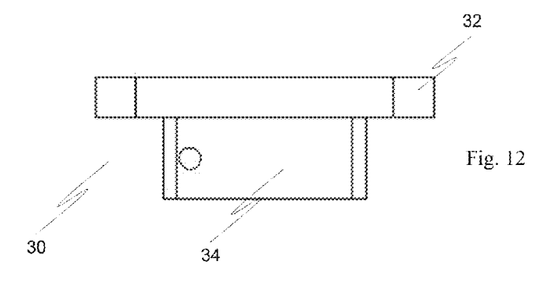
FIGS. 12-14 illustrate environmental perspective views of an exemplary realization of a mounting standard as depicted in FIGS. 10-11.
Figure 13:
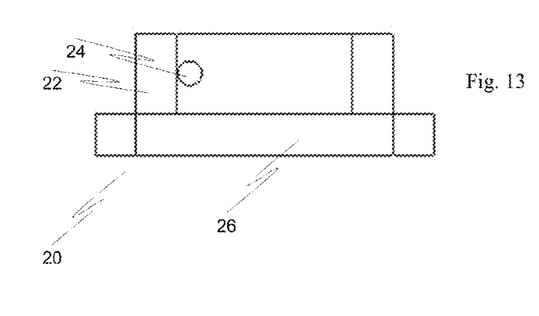
Figure 14:
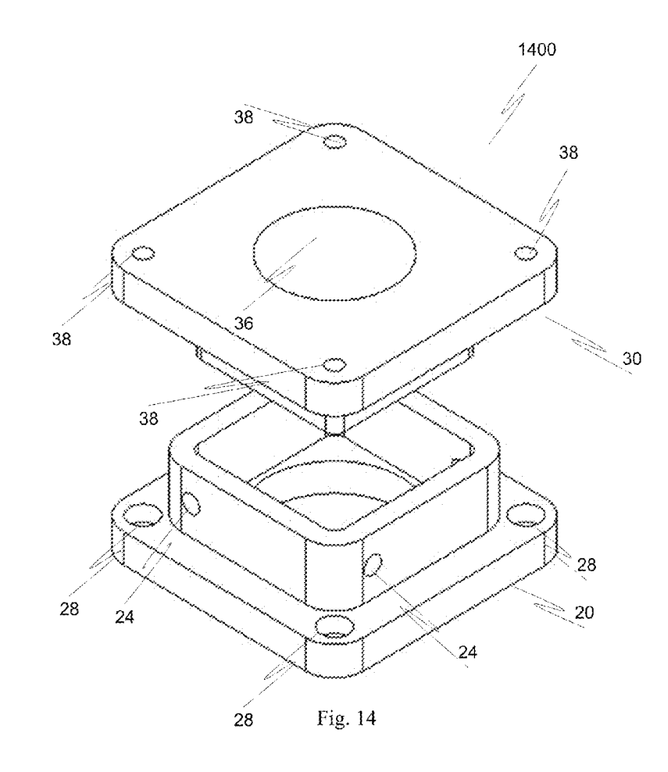

FIGS. 12-14 illustrate environmental perspective views of an insert 12 and flange 13 that form the mechanical coupling 1400 for an exemplary mechano-optical coupling (FIG. 14).

According to various embodiments, a coupling 1400 is provided, the coupling being adapted for attachment with at least the port switcher of the present invention, in addition to any other module(s). In one embodiment, the coupling 1400 generally comprises an insertable male portion or insert 30 and a female or receiving flange or portion 20. The insertable portion 30 is generally comprised of a substantially rectilinear flange portion 32 having a predetermined height and integrally connected to a raised portion 34. In one embodiment, the raised portion 34 comprises a predetermined height greater than the predetermined height of the flange portion 32. However, one of ordinary skill in the art will recognize that insertable portions 30 may be provided, the insertable portions 30 comprising any number of ratios between the height of the flange portion 32 and the raised portion 34.

In various embodiments, the insertable portion 30 comprises at least one aperture 36 through which at least some light is allowed to pass. An aperture 36 may be comprised of a through-hole fitted with any number of known glasses or plastics, depending upon an amount of desired transmission through the aperture 36. One of skill in the art will recognize that various known glasses and/or plastics may be provided so as allow/prevent various wavelengths of light from passing through apertures 36 of the present invention. Additionally, the aperture may not be filled with glass or plastic, and could be left empty.

In one embodiment, an insertable portion 30 comprises a plurality of through holes 38 suitable for mounting the insertable portion to one or more of the various modules and/or receiving portions 20 and/or various additional components. Through holes 38 may comprise threaded or non-threaded apertures adapted for receiving fastening components including, but not limited to, screws, bolts, nails, pins, and various similar anchoring and fastening members.

In various embodiments, a coupling 1400 comprises a receiving portion 20 adapted for receiving the insertable portion 30. In one embodiment, the receiving portion 20 is generally comprised of a substantially rectilinear flange portion 26 having a predetermined height and integrally connected to a raised female portion 22. In one embodiment, the raised female portion 22 comprises a predetermined height greater than the predetermined height of the flange portion 26. However, one of ordinary skill in the art will recognize that receiving portions 20 may be provided, the receiving portions 20 comprising any number of ratios between the height of the flange portion 26 and the raised female portion 22. In one embodiment, inner dimensions (e.g. length and width) of a raised female portion 22 are at least as large as corresponding outer dimensions of a raised portion 34.

Receiving portions 20 of the present invention may further comprise through holes or apertures 28 for mounting the receiving portion 20 onto additional components modules and/or mounting components and devices (e.g. an insertable portion 30) to the receiving portion 20. Through holes or apertures 28 may be threaded or non-threaded apertures for receiving or accommodating various additional devices including, but not limited to, various fastening devices. Raised female portions 22 may further comprise one or more through holes 24. In one embodiment, one or more through holes 24 are provided, the through holes 24 adapted to receive a set screw (not shown) for securing an insertable portion 30 and a receiving portion 20 in a desired arrangement.

In various embodiments, receiving portions 20 comprise one or more apertures adapted for the transmission of at least certain wavelengths of light. In one embodiment, apertures provided on a receiving portion correspond to and/or align with paths of light travel through corresponding apertures in an insertable portion 30. As with aperture 36, the aperture may be filled with one or more of plastic, glass or be left empty.

In various embodiments, intersections or corners of various portions of the insertable portion and/or receiving portion 20 are rounded or finished so as to reduce the presence of sharp corners or features.

As discussed above, one alternative exemplary mechano-optical coupling standard similar to that illustrated in FIG. 14 could be a polygonal insert and a matching flange where after insertion, the two parts can be securely fastened together (with a bolt or other fastener or fastening system, for example). As will be appreciated, numerous other geometric configurations of the insert and flange can be utilized provided the components can be securely fastened together. For example, in various embodiments, couplings 1400 of the present invention are adapted to be selectively positioned. For example, couplings may be oriented with respect to additional components at 90 degree increments. Furthermore, receiving portions 20 and insertable portions 30 of the present invention may be oriented and/or offset with respect to one another at 90 degree increments. In one embodiment, the ability to selectively position or orient portions of a coupling 1400 is enabled by the geometric configuration of the portions. For example, a raised female portion 22 and insertable portion 30 may comprise a geometry that allows for rotation of the raised female portion 22 and insertable portion 30 with respect to one another solely in 90 degree increments. In one embodiment, the respective geometries comprise polygons adapted to mate with another at specific locations, the specific locations being offset from one another by 90 degrees of rotation. Polygons may comprise, but are not limited to, squares, rectangles, diamonds, L-shaped features, and various similar objects having one or more right angles. Thus, in various embodiments, couplings 1400 are provided having the ability to be accurately positioned and re-positioned in predetermined positions. In various embodiments, couplings provide markings or feedback features adapted for displaying information related to the orientation of the coupling to a user. For example, where a square coupling is provided, various markings can be optionally placed on the coupling to indicate information related to orientation (e.g. a 1st, 2nd, 3rd, and 4th position defined by 0, 90, 180, and 270 degrees of rotation, respectively).

Figure 15:
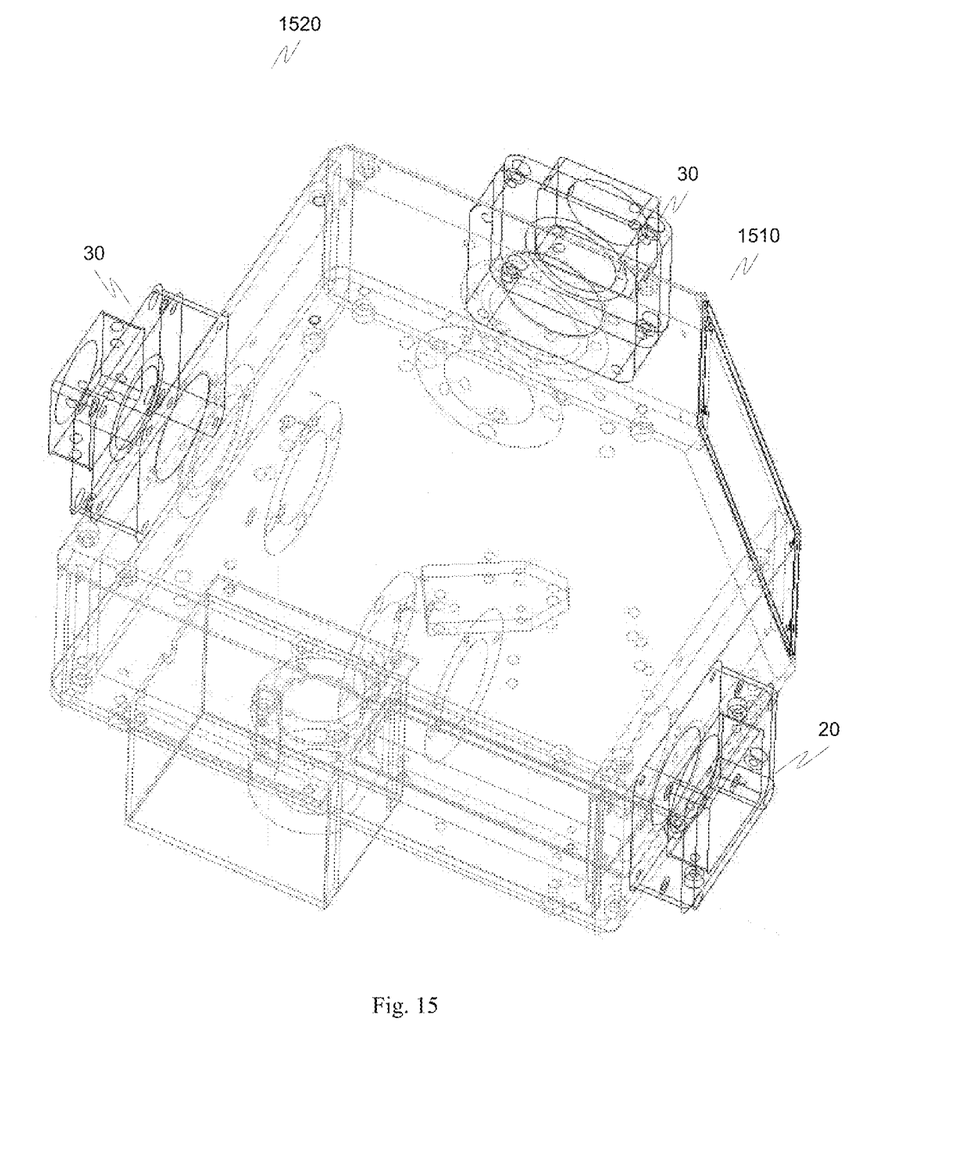
FIG. 15 illustrates an environmental perspective view of a laser scanner module.

FIG. 15 illustrates an environmental perspective view of a port switcher module 1510. The flange 20 acts as an optical input for, for example, a relay system. The image is relayed to one of two inserts 30 based on the position of a mirror housed inside the port switcher module 1510.

Figure 16:
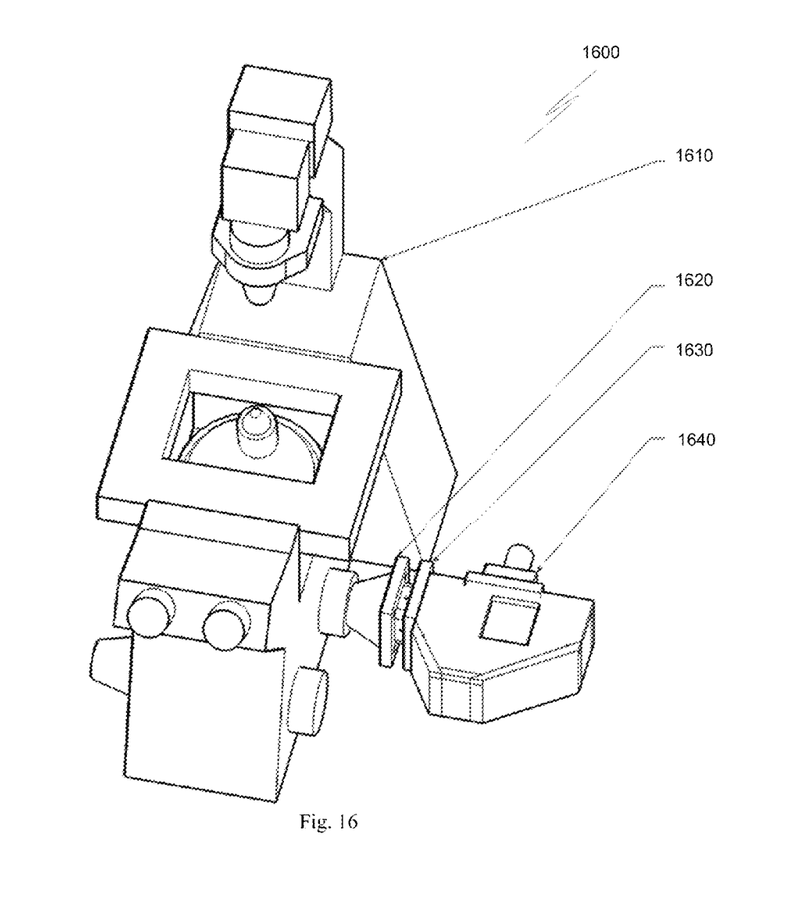
FIG. 16 illustrates an environmental perspective view and a FIG. 17 a graphical representation of a simple system built from only three modules.
Figure 17:
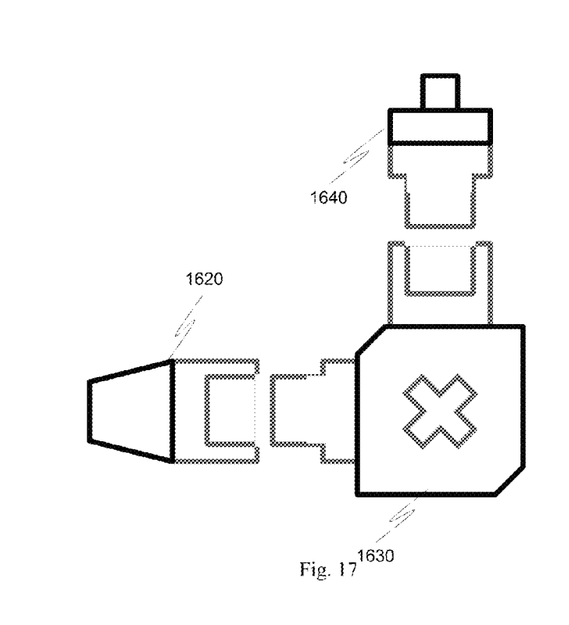

FIGS. 16 and 17 illustrate an environmental perspective view and a graphical representation, respectively, of a simple combination of modules to form a laser scanner 1600. This combination would enable photo-ablation experiments, for example. The combination forms a laser scanning device attached to the document port of a microscope 1610. The exemplary modules include a c-mount adapter 1620 that couples the laser scanner 1630 to the microscope. A fiber laser input module 1640 allows a fiber to be attached to the laser scanner as an input.

Figures 18, 19:
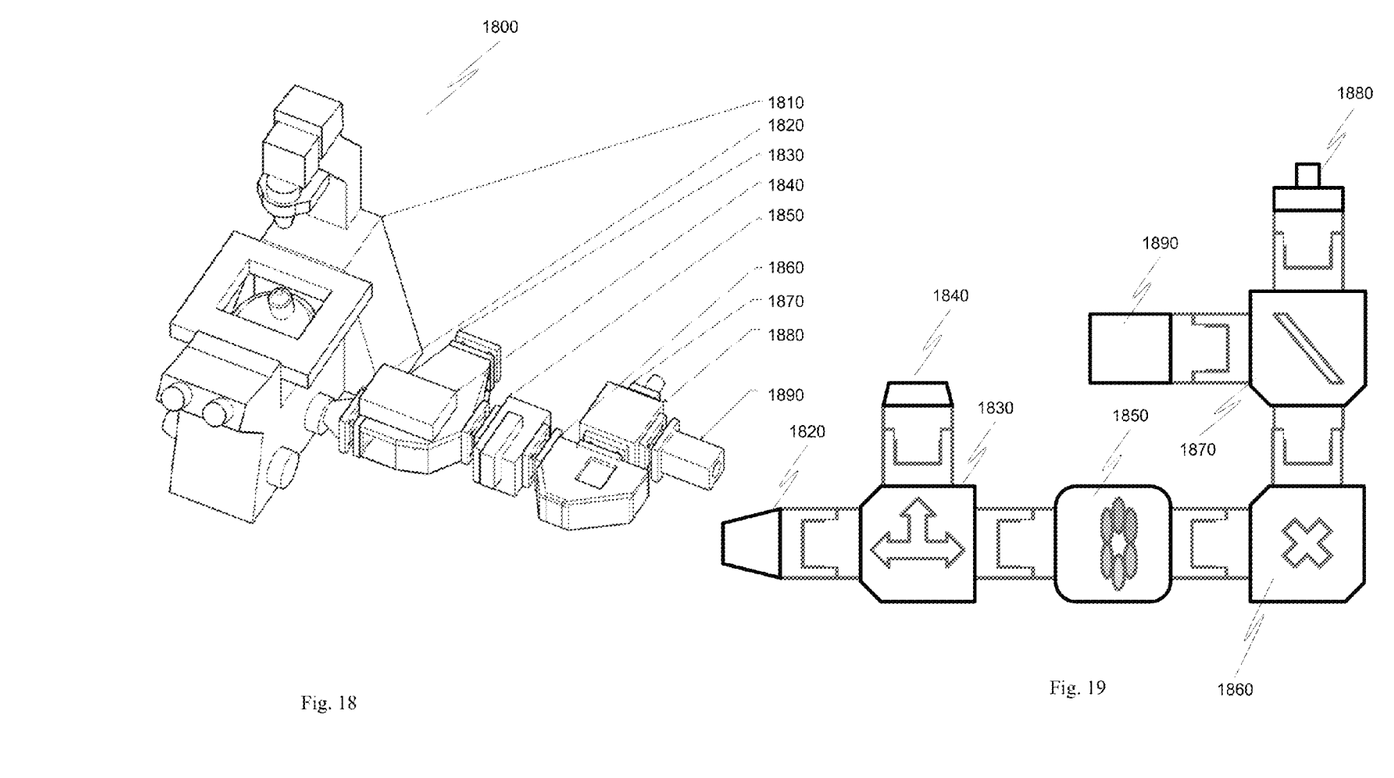

FIGS. 18 and 19 illustrate an environmental perspective view and a graphical or schematic representation, respectively, of a complex combination of modules to form an advanced laser scanning device 1800. This combination would enable photo-bleaching experiments, scanning confocal, or fluorescence correlation spectroscopy (FCS) during live imaging. The device is attached to the document port of a microscope 1810 using a c-mount adapter module 1820. A fast port switching module 1830 switches between a c-mount adapter for a camera 1840 and the rest of the device. A filter wheel module 1850 can select the emission wavelength desired. The laser scanner 1860 acts as a scanner and de-scanner for fluorescence. The input laser light is split using a dichroic module 1870 from the laser fiber input 1880 and a PMT detector module 1890. Such a combination of modules would allow several different advanced laser scanning techniques to be used. It can also be seen that changing the location of the modules or by adding other modules the functionality can change as well.

The exemplary techniques illustrated herein are not limited to the specifically illustrated embodiments but can also be utilized with the other exemplary embodiments and each described feature is individually and separately claimable. In addition, the inserts and flanges illustrated herein can be affixed to any type of module, connector, mount, or in general any element associated with an optical system and/or imaging system and/or microscope system.

The systems of this invention also can cooperate and interface with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device such as PLD, PLA, FPGA, PAL, any comparable means, or the like.

Furthermore, the disclosed system may use control methods and graphical user interfaces that may be readily implemented in software using object or object-oriented software development environments that provide portable source code that can be used on a variety of computer or workstation platforms. Alternatively, the disclosed control methods may be implemented partially or fully in hardware using standard logic circuits or VLSI design. Whether software or hardware is used to implement the systems in accordance with this invention is dependent on the speed and/or efficiency requirements of the system, the particular function, and the particular software or hardware systems or microprocessor or microcomputer systems being utilized.

It is therefore apparent that there has been provided, in accordance with the present invention a modular laser scanning device. While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A laser scanning system comprising:
   a laser scanner contained in a separate mechanical entity; and
   one or more mechano-optical couplings, the one or more mechano-optical couplings connecting the laser scanner to one or more optical modules, respectively, and one or more additional mechano-optical couplings connecting the laser scanner to a standard microscope, each mechano-optical coupling including an insertable male portion and a receiving flange, the insertable male portion including a substantially polygonal flange portion having a predetermined height and integrally connected to a raised portion, the raised portion comprising a predetermined height greater than the predetermined height of the flange portion, the insertable male portion further including at least one aperture, the receiving flange including a substantially polygonal flange portion having a predetermined height and integrally connected to a raised female portion, the raised female portion including a predetermined height greater than the predetermined height of the flange portion, the receiving flange further including at least one aperture, the insertable male portion and the receiving flange joinable with an image plane located exactly between the insertable male portion and the receiving flange.

2. The system of claim 1, wherein the mechano-optical couplings are a mechanical and optical standard for coupling the laser scanner and the one or more additional optical modules.

3. The system of claim 2, wherein the mechano-optical couplings are a right angle polygonal flange and are adapted to attach the laser scanner to the standard microscope.

4. The system of claim 3, wherein the laser scanner is adapted to attach to a document port of the standard microscope.

5. The system of claim 3, wherein the laser scanner is adapted to attach to an EPI port of the standard microscope.

6. The system of claim 3, further comprising optics adapted to couple to the standard microscope.

7. The system of claim 3, further comprising separate modules containing optics for one or more of adjusting the functionality of the laser scanner, combining multiple scanners and multiple techniques.

8. The system of claim 7, wherein one module comprises fiber coupling mechanics and optics for coupling to a laser.

9. The system of claim 7, wherein one module comprises a path switcher to split the optical pathway into several pathways.

10. The system of claim 9, wherein the path switcher contains a fast galvanometer.

11. The system of claim 9, wherein the path switcher provides an imaging bypass for attaching a camera to the same port as the laser scanner.

12. The system of claim 7, wherein one module is a dichroic path splitter that spectrally splits the optical path.

13. The system of claim 7, wherein one module is a spherical aberration correction device.

14. The system of claim 7, wherein one module is a filter wheel.

15. The system of claim 7, wherein one module is a detector or a PMT.

16. The system of claim 2, wherein the standard allows rotational freedom only on 90 degree intervals.

17. The system of claim 1, further comprising one or more markings placed on each mechano-optical coupling to indicate information related to orientation for $1^{st}$ through 4th positions defined by 0, 90, 180, and 270 degrees of rotation, respectively.

18. A scalable modular system that separates optical functions applicable to a laser scanning device into separate mechanical entities, each mechanical entity being combinable in different orders and amounts to enable different functionality in the laser scanning system, wherein the scalable modular system comprises a plurality of optical modules, each optical module coupleable to the laser scanning device via a mechano-optical coupling, the mechano-optical coupling including an insertable male portion and a receiving flange, the insertable male portion including a substantially polygonal flange portion having a predetermined height and integrally connected to a raised portion, the raised portion comprising a predetermined height greater than the predetermined height of the flange portion, the insertable male portion further including at least one aperture, the receiving flange including a substantially polygonal flange portion having a predetermined height and integrally connected to a raised female portion, the raised female portion including a predetermined height greater than the predetermined height of the flange portion, the receiving flange further including at least one aperture, the insertable male portion and the receiving flange joinable with an image plane located exactly between the insertable male portion and the receiving flange.

19. The system of claim 18, wherein the mechano-optical coupling is a standard for coupling the optical modules, and includes the polygonal flange and receiving flange that are rigidly combined.

20. The system of claim 19, wherein an image plane in the standard lies directly between two combined optical modules.

21. The system of claim 19, wherein the polygon is a square.

22. The system of claim 19, further comprising a defined field and incident angle for the standard.

23. The system of claim 18, wherein the plurality of optical modules include interconnectable modules including one or more of a male c-mount adapter, a female c-mount adapter, a fiber input, a detector, a fast port switcher, a dichroic beam splitter, a spherical aberration correction device and a filter wheel.

24. The system of claim 18, wherein the mechano-optical coupling allows each optical module to be combined in different orders and amounts.

25. The system of claim 24, wherein a port switcher is connected to a plurality of the mechano-optical couplings.

* * * * *